United States Patent [19]
Gambell et al.

[11] Patent Number: 5,925,798
[45] Date of Patent: *Jul. 20, 1999

[54] THORIA CATALYST

[75] Inventors: James William Gambell, Ballwin, Mo.; Paul Ho Liu, Shanghai, China; Jerry Rudolph Ebner, St. Peters, Mo.

[73] Assignee: Solutia Inc., St. Louis, Mo.

[*] Notice: This patent issued on a continued prosecution application filed under 37 CFR 1.53(d), and is subject to the twenty year patent term provisions of 35 U.S.C. 154(a)(2).

[21] Appl. No.: 08/955,314

[22] Filed: Oct. 21, 1997

Related U.S. Application Data

[63] Continuation of application No. 08/401,045, Mar. 8, 1995, abandoned.

[51] Int. Cl.$^6$ .......................... C07C 43/275; B01J 23/12
[52] U.S. Cl. .......................... 568/635; 568/58; 568/632; 502/300; 423/252
[58] Field of Search .................... 502/349, 300; 423/252; 568/58, 632, 635

[56] References Cited

U.S. PATENT DOCUMENTS

| | | | |
|---|---|---|---|
| 2,436,125 | 2/1948 | Spence et al. | 252/204 |
| 3,363,002 | 1/1968 | Craggs | 260/612 |
| 3,429,816 | 2/1969 | Giolito et al. | 252/52 |
| 3,907,696 | 9/1975 | Jackson et al. | 252/73 |
| 3,966,626 | 6/1976 | Jackson et al. | 252/73 |
| 3,989,761 | 11/1976 | Gross | 260/620 |
| 4,000,203 | 12/1976 | Gross et al. | 260/620 |
| 4,008,254 | 2/1977 | Gross et al. | 260/346.2 |
| 4,008,266 | 2/1977 | Intille | 260/475 |
| 4,009,185 | 2/1977 | Fishel | 260/346.2 |
| 4,013,694 | 3/1977 | Fishel | 260/346.2 |
| 4,035,428 | 7/1977 | Fishel et al. | 260/620 |
| 4,054,533 | 10/1977 | Watson | 252/73 |
| 4,085,143 | 4/1978 | Holmes | 260/515 R |
| 4,088,698 | 5/1978 | Fishel et al. | 260/609 |
| 4,092,364 | 5/1978 | Smith | 260/612 R |
| 4,331,656 | 5/1982 | Bouillon et al. | 424/70 |
| 4,407,735 | 10/1983 | Sawamura | 502/10 |
| 4,465,889 | 8/1984 | Anthony et al. | 585/640 |
| 4,490,567 | 12/1984 | Drake | 585/324 |
| 4,491,640 | 1/1985 | Sadamori et al. | 502/242 |
| 4,532,230 | 7/1985 | Colmenares et al. | 502/344 |
| 4,596,680 | 6/1986 | Jost et al. | 560/424 |
| 4,891,448 | 1/1990 | Garces et al. | 568/628 |
| 4,898,982 | 2/1990 | Hussman | 568/58 |
| 4,978,811 | 12/1990 | Koster et al. | 568/734 |
| 5,288,922 | 2/1994 | Buske et al. | 568/635 |

FOREIGN PATENT DOCUMENTS

| | | |
|---|---|---|
| 0317208A2 | 5/1989 | European Pat. Off. . |
| 1603748 | 7/1971 | France . |
| 1810179 | 7/1969 | Germany . |
| 495143 | 11/1938 | United Kingdom . |
| 911246 | 5/1960 | United Kingdom . |
| 1236389 | 6/1971 | United Kingdom . |

OTHER PUBLICATIONS

Brey, Jr., et al., "Preparation and Properties of Active Thorium Oxide from Thorium Hydroxide", *Journal of Catalysis* 3, pp. 303–311 (1964), From the Department of Chemistry, University of Florida, Gainesville.

Abstract: FR 1603748A (19680917) discloses the catalyst is obtained by incorporating in a inert support, a thorium compound, which decomposes to the oxide on heating at 200–600 degrees C, pref. between 300 and 400 degrees C.

Comptes Rendus, Hebdomadaires, Des Seances, De Lacademie Des Sciences, En Date Due 13 Juillet 1835, vol. 151, Juillet–Dec. 1910 Paris, Authier–Villars.

Journal of the American Chemical Society vol. 71, May 1949, 1806–1816, On Selective Catalysis, George Maria Schwab and Elly Schwab–Agallidis.

S. Karuppannasamy, et al., "Investigations of Phenol Decomposition on Thoria Catalysts", Proc. Natl. Symp. Catal., 4$^{th}$, 1978, pp. 443–450.

E. Briner, et al., "Catalytic Dehydration of Phenols; Influence and Nature of the Position of Substituted Groups", Heb. Chin. Acta., vol. 15, Aug. 1932, pp. 1234–1241.

Karuppannasarny et al., "Investigations of Phenol Decomposition on Thoria Catalysts", Department of Chemistry, Indian Institute of Technology, Madras–600 036(India), Proc. Natl. Symp. Catal., 4$^{th}$ Edition, 1978, pp. 443–450.

Abstract: 94–46533v Investigations of Phenol Decomposition on Thoria Catalysts, S. Karuppannasamy, et al., (Dep. Chem., Indian Inst. Technol., Madras, 600 036 India). Proc. Natl. Symp. Catal., 4$^{th}$ 1978 (Pub. 1980), 443–50 (Eng.) Indian Inst. Technol.: Bombay, India.

Abstract: "Catalytic Phenyl Ethers Production", Patent Assignee: Midland–Yorkshire Tar Dis, GB 1236389.

Alvin B. Stiles, University of Delaware, "Catalyst Supports and Supported Catalysts Theoretical and Applied Concepts", Copyright 1987 Butterworth Publishers, Index and p. 5.

Ernest M. Levin, et al., "Phase Diagrams for Ceramists", Copyright 1956 by The American Ceramic Society, Metal Oxide Systems, p. 68.

Communication of Paul Sabatier and A. Mailhe, "Catalytic Preparation of Phenolic Oxides and Diphenylene Oxides", C.R. Acad. Sci., vol. 151 (1910), pp. 492–494 (Translation from French).

(List continued on next page.)

*Primary Examiner*—Bekir L. Yildirim
*Attorney, Agent, or Firm*—Fitzpatrick, Cella, Harper & Scinto

[57] ABSTRACT

A more reactive thoria catalyst for the production of diaryl ethers from aromatic compounds, a process for making the catalyst and the use of the catalyst is taught. The thoria catalyst has a specified surface area, density and average crystal size.

37 Claims, No Drawings

OTHER PUBLICATIONS

Report by Mr. Paul Sabatier and Mr. A. Mailhe, "Organic Chemistry: Carvacrol Ethers", Comptes rendus [Reports] of the Academy of Sciences, Proceedings of the meeting held on Feb. 23, 1914, pp. 608–612 (Translation from French).

Report by Mr. Paul Sabatier and Mr. A. Mailhe, "Organic Chemistry: Catalytic Preparation of Phenolic Oxides and Diphenylenic Oxides", Comptes rendus [Reports] of the Academy of Sciences, Proceedings of the meeting held on Aug. 22, 1910, pp. 492–494 (Translation from French).

Report by Mr. Paul Sabatier and Mr. A. Mailhe, "Organic Chemistry**Catalytic Preparation of Phenolic and Diphenylenic Oxides: Mixed Oxides", Comptes rendus [Reports] of the Academy of Sciences, Proceedings of the meeting held on Jul. 22, 1912, vol. 155, No. 4 (second six months), pp. 260–262 (Translation from French).

Francois Claes, et al., "No. 188.—Quantitative Kinetics in Heterogeneous Catalysis: Dehydration of Phenols on Thoria", (Physical Chemistry Laboratory, University of Louvain, Belgium, Manuscript received on Apr. 3, 1962), Bull. Soc. Chim. Franc., vol. 964, pp. 1042–1046, Series 5 (1962)—Memoranda presented to the Chemical Society (Translation from French).

Abstract: 85–50883 MITC * E14 84–315126/51 *J5 9196–835–A; Di:phenyl ether(s) prepn. with high selectivity—by contacting phenol(s) with titanium oxide or zirconium oxide in the vapour phase.

Abstract: "Thorium Oxide Catalyst for Selective De–Hydration—of Secondary Alcohols t alpha", Patent Assignee: Inst Francais Du Petrole, FR 1603748.

Abstract: OLS 1, 810, 179; Diaryl ethers in which each aromatic nucleus is substituted by at least one secondary or tertiary . . . , 21.11.68. P 1810179.6 (22.11.67. G.B. 53181/67) Midland–Yorkshire Tar Distillers Ltd. (24.7.69). C07c.

"Preparation Catalytique des oxydes Phenoliques et des oxydes diphenyleniques"; P. Sabatier, et al.; Comptes Rendus, vol. 151, pp. 492–494, (1910); No translation.

"Sur la deshydratation catalytique des phenols"; E. Briner, et al.; Helvetica Chemica Acta; vol. 15, pp. 1234–1241, (1932); No translation.

"La cinetique quantitative en catalyse heterogene. La deshydratation des phenols sur la thorine"; F. Claes, et al.; Bull. Soc. Chim Fr. (1964), pp. 1042–1046; No translation.

"Reactions of Phenols and Alcohols Over Thoria"; S. Karuppannasamy, et al.; J. of Catalysis 63; pp. 433–437 (1980).

"Reactions of Phenols and Alcohols Over Thoria: Mechanism of Ether Formation"; S. Karuppannasamy, et al.; J. Of Catalysis 66; pp. 281–289 (1980).

*Catalysis in Organic Syntheses*, Edited by W. H. Jones (1980); pp. 119–132.

THORIA CATALYST

This application is a continuation of application Ser. No. 08/401,045 filed Mar. 8, 1995, now abandoned.

BACKGROUND OF THE INVENTION

This invention relates to a thoria catalyst. More particularly, this invention relates to an improved, more reactive thoria catalyst for the production of diaryl ethers from aromatic compounds and to the process for producing the more reactive catalyst.

DESCRIPTION OF THE PRIOR ART

Diaryl ethers such as diphenyl oxide are useful as high temperature solvents and as components in heat transfer fluids and perfumes. In addition, diaryl ethers are intermediates in processes for is preparing flame retardants and surfactants.

The production of diphenyl oxide by the caustic hydrolysis of chlorobenzene is disclosed in U.S. Pat. No. 4,092,364, by contacting phenol with aluminum is disclosed in U.S. Pat. No. 4,360,699 and by the pyrolysis of diaryl carbonates is disclosed in U.S. Pat. No. 4,596,680.

However, it is more desirable to prepare diaryl ethers by the dehydration of phenols. The dehydration was first reported by P. Sabatier and A. Mailhe (Compt. Rend., 151, 1910, 492–494). They passed phenol over a thoria catalyst at 410° C. and atmospheric pressure to obtain diphenyl oxide and dibenzofuran as a byproduct.

More recently, F. Claes and J. C. Jungers (Bull. Soc. Chim. Fr., 1962, 1042) evaluated the kinetics of phenol dehydration to diphenyl ether over thoria supported on pumice.

In addition to the work of Claes and Jungers, British Patent 911,246 discloses the reversible reaction for the dehydration of phenols to diphenyl oxide over thoria supported on alpha-alumina and over unsupported thoria. The reaction was carried out in the vapor phase at substantially atmospheric pressure and at an elevated temperature between 300° C. and 550° C. The preferred temperature was the highest temperature possible consistent with a reasonably slow rate of catalyst deactivation such as, for example, between 450° C. and 475° C. The catalyst was regenerated by passing an air steam through the reactor at a temperature of 500° C. for a period of approximately 2 hours until the localized heating caused by the removal of carbon could no longer be detected.

U.S. Pat. No. 4,898,982 discloses the dehydration of phenol to diaryl oxide and thiophenol to diaryl sulfide over thoria deposited on a neutral support such as pure silica, pure zirconia, carbon or asbestos.

There are few examples of catalysts other than thoria which successfully dehydrate phenols to diaryl ethers. One example is disclosed in U.S. Pat. No. 5,288,922 wherein diaryl ether is prepared by the dehydration of a hydroxy-substituted aromatic compound, such as phenol, over a zeolite catalyst such as a dealuminated acidic mordenite catalyst.

It is, thus, an object of this invention to provide an improved, more reactive thoria catalyst for use in the dehydration/hydration reactions for aromatic compounds such as phenol, diaryl ether compounds such as diphenyl ethers and other similar compounds. It is a further object of this invention to provide a process for the production of the improved thoria catalyst.

SUMMARY OF THE INVENTION

This invention is directed to an improved, more reactive thoria catalyst which may be unsupported or supported. The unsupported thoria catalyst has a surface area less than 62 square meters/gram (62 m$^2$/g), a true density greater than 8.5 grams/cubic centimeter (8.5 g/cc) and an average crystal size greater than 75 angstroms (75 Å).

This invention is also directed to a process for producing a thoria catalyst comprising the steps of (a) preparing a formed structure from a high surface area thoria precursor and (b) calcining the formed structure at a temperature greater than about 600° C. for a time sufficient to achieve the desired physical properties.

The invention is further directed to a method for producing diaryl ethers comprising passing an aromatic compound over a thoria containing catalyst at a temperature between about 400° C. and about 475° C., the thoria containing catalyst having a thoria portion which has a surface area less than 62 m$^2$/g, a true density greater than 8.5 g/cc and an average crystal size greater than 75 angstroms.

DESCRIPTION OF THE PREFERRED EMBODIMENTS

In accordance with the present invention, an improved, more reactive thoria catalyst is provided. The catalyst may be unsupported or supported. The unsupported thoria catalyst has a surface area less than 62 square meters/gram (62 m$^2$/g), preferably less than 60 square meters/gram (60 m$^2$/g) and more preferably less than 55 square meters/gram (55 m$^2$/g); a true density greater than 8.5 grams/cubic centimeter (8.5 g/cc) and preferably greater than 8.6 grams/cubic centimeter (8.6 g/cc); and an average crystal size greater than 75 angstroms (75 Å) and preferably greater than 90 angstroms (90 Å).

The surface area of the catalyst may be measured by BET (Brunauer, Emmett & Teller) Isotherm techniques.

True density is defined as the density of the solid phase exclusive of the space involving porosity, that is the solid phase excluding the pores in the surface. The true density is measured by helium pyncnometry. In contrast to true density, skeletal density which is measured by mercury porosimetry excludes the surface pores only to the extent that mercury can penetrate the pore, thus all pores are not measured and excluded from the calculation of density.

Average crystal size may be determined according to known procedures. All samples were first tested and compared to Powder Diffraction File 42-1462 (PDF 42-1462) to determine that the samples were thorium oxide (ThO$_2$). The average crystal size was measured by x-ray diffraction analysis, measuring from the [220] reflection from the thorium oxide. The [220] reflection (two theta of 45.8 degrees) was used for the crystallite size determination because it has less overlap with other peaks than the other reflections in the x-ray diffraction pattern. The crystallite size was calculated using the Scherrer Equation:

$$\text{Crystallite size} = K \times (\text{x-ray wavelength Å})/\beta \times \cos(\theta) \quad (1)$$

where $$\beta = (\text{FWHM} - \text{intrinsic line width}) \times (\pi/180) \quad (2)$$

and FWHM means full width at half-peak maximum, that is, the measured width of the peak at one-half its height. The measured size may be adjusted for instrumental broadening, but this is not a significant adjustment to the measurement as the measured peaks are greater than 1-degree in breadth and the instrumental broadening is less than 0.05-degree. The measurement is repeated several times to determine the average crystal size.

When a supported thoria catalyst is used, these physical properties are still important. The average crystal size may still be measured in accordance with the method described above. Use of the BET (Brunauer, Emmett & Teller) Isotherm technique for the measurement of the surface area of the thoria portion of the supported catalyst will be compromised by the presence of the support and may be difficult to interpret unless the support material has a very low surface area which can be ignored. True density of the thoria portion of the supported catalyst can be inferred from the difference between the measured true density of the composite supported catalyst which contains both support and thoria and the measured true density of the support alone.

This thoria catalyst is particularly useful for the dehydration of phenol as it unexpectedly yields higher conversions to diphenyl oxide than the thoria catalyst of the prior art. An unexpected aspect of this invention was the discovery that preparation of a catalyst with a decreased surface area resulted in an increase in the activity of the catalyst and an increase in the conversion of phenol to diphenyl oxide.

It is expected that the activity of a catalyst, and the resulting conversion rates in a process which uses it, would increase if the surface area of the catalyst were increased. As a result, in the past the process for the production of thoria catalyst has been designed to maximize the catalyst surface area and to minimize the calcining temperature. The catalyst was, thus, calcined at or below a temperature of approximately 550° C. to prepare it for use in a process. It has now been discovered that the opposite is true. It has been discovered that a higher temperature calcination and a reduced surface area is preferred. When the thoria catalyst is calcined at a temperature greater than about 600° C., preferably at a temperature greater than about 650° C., and more preferably at a temperature greater than about 700° C., the surface area of the catalyst, as measured by BET Isotherm techniques, decreases when compared to the surface area of the thoria catalyst calcined at a temperature of about 550° C. and surprisingly the conversion of phenol to diphenyl oxide increases.

The catalyst of this invention may be advantageously used in processes for the dehydration of hydroxy-substituted aromatic compounds to diaryl ether compounds. The catalyst creates a high conversion of the hydroxy-substituted aromatic compounds to provide a high yield of diaryl ethers. As a further advantage, another benefit of this catalyst, the higher activity and resulting higher conversion and yield may be realized even when the catalyst is used at typical dehydration process temperatures for the reaction of phenol of 400° C. to 475° C.

The preferred use for the thoria catalyst of this invention is in a process for the dehydration of phenol to produce diphenyl ether. The catalyst may, however, be used in other similar reactions, including the hydration of diphenyl ether to produce phenol. It may also be used in processes for the dehydration of other hydroxy-substituted compounds including α- and β-hydroxy-substituted fused aromatic ring systems. Apart from the hydroxy substituent, the compounds may be unsubstituted, as in phenol or naphthol, or they may be further substituted with at least one alkyl group containing from 1 to about 10 carbon atoms, preferably from 1 to 3 carbon atoms, or substituted with at least one alternative substituent which is inert to the dehydration coupling reaction. Suitable inert substituents include cyano, amino, nitro, carboxyl, ester, alkoxy, and phenoxy moieties. It is also possible for the hydroxy-substituted aromatic compound to be substituted with both an alkyl substituent and one of the alternative inert substituents. Each of the alkyl substituents or alternative inert substituents is preferably attached to an aromatic ring carbon atom which is located in a meta or para position relative to the hydroxy moiety.

The following compounds are illustrative of, but do not limit, the compounds with which the catalyst of this invention may be used. The products formed from each compound are shown in parenthesis. Examples of suitable phenols include unsubstituted phenol (diphenyl ether), m-cresol (3,3'-dimethyldiphenyl ether), p-cresol (4,4'-dimethyldiphenyl ether), 3,4-xylenol (3,3',4,4'-tetramethyldiphenyl ether), 3,5-xylenol (3,3',4,4'-tetramethyldiphenyl ether), 3,4,5-trimethylphenol (3,3',4,4', 5,5'-hexamethyldiphenyl ether) and corresponding compounds in which one or more of the methyl substituents are replaced by an ethyl, propyl or butyl substituent. Examples of α- and β-hydroxy-substituted fused aromatic ring systems include α- and β-naphthol (dinaphthyl ether) and 5-tetralinol (ditetralin ethers). As discussed above, the substituents on the above compounds may also be replaced by any of the alternative inert substituents listed above such as the cyano, amino and nitro moieties. One skilled in the art may find other α- and β-hydroxy-substituted fused aromatic ring systems which may be reacted in processes utilizing the catalyst of this invention. Preferably the catalyst is used in processes for the dehydration of unsubstituted phenol or substituted phenol wherein the substituent is methyl or ethyl. More preferably, the catalyst is used in processes for the dehydration of unsubstituted phenol or cresol and the most preferred process is the dehydration of phenol to produce diphenyl oxide.

While the thoria catalyst of this invention is used as an unsupported thoria catalyst, the thoria catalyst is also suitable for use as a supported catalyst. Suitable support materials preferably have no or very weak acidic or basic properties. Suitable support materials include alpha-alumina, pure silica, pure zirconia, silicon carbide, carbon, asbestos, quartz cordierite, mullite and beta spodumene. The term "pure" means that the support material contains less than 1000, and preferably less than 500, parts per million of metallic impurities, calculated as the elemental metals.

When a supported catalyst is used, the thoria content of the thoria catalyst of this invention is in the range of from about 1% to about 70% by weight, preferably from about 10% to about 60% by weight, and most preferably about 50% by weight, calculated as thorium oxide ($ThO_2$) based upon the total weight of the catalyst. The physical properties of the thoria portion of the supported thoria catalyst are equal to the physical properties of the unsupported thoria catalyst. Thus, the thoria portion of the supported thoria catalyst of this invention has a surface area less than 62 square meters/gram (62 $m^2$/g), preferably less than 60 square meters/gram (60 $m^2$/g) and more preferably less than 55 square meters/gram (55 $m^2$/g); a true density greater than 8.5 grams/cubic centimeter (8.5 g/cc) and preferably greater than 8.6 grams/cubic centimeter (8.6 g/cc); and an average crystal size greater than 75 angstroms (75 Å) and preferably greater than 90 angstroms (90 Å).

This invention is also directed to a process for producing a thoria catalyst comprising the steps of (a) preparing a formed structure from a high surface area thoria precursor and (b) calcining the formed structure at a temperature greater than about 600° C., preferably at a temperature greater than about 650° C. and more preferably at a temperature greater than about 700° C., for a time sufficient to achieve the desired physical properties.

For the production of the unsupported thoria catalyst of this invention, a mixture was prepared from a high surface area thoria precursor in the form, for example, of thorium oxide ($ThO_2$) and graphite, which acts as a lubricant when the catalyst mixture is formed into the desired shape. The mixture was then compressed into tablets. The tablets were placed in a furnace and heated to a temperature greater than about 600° C., preferably to a temperature greater than about 650° C. and more preferably to a temperature greater than about 700° C. The temperature in the furnace was raised slowly, for example at a rate of 1° C. to 10° C. per minute to evenly heat the catalyst tablets. After reaching the desired temperature, the furnace was maintained at that temperature for a period of time sufficient to complete the calcining of the catalyst tablets, to remove all of the graphite and to achieve the desired physical properties of the catalyst—a thoria catalyst having a surface area less than 62 $m^2/g$, a true density greater than 8.5 g/cc and an average thoria crystal size greater than 75 Å. The desired temperature will typically be maintained for a period of about 1–9 hours and preferably about 5 hours; however, shorter or longer times may be required to complete the calcining of the catalyst tablets. Following the completion of the calcining, the furnace was cooled slowly to ambient temperature. The calcined thoria catalyst pellets were white in color indicating a complete calcination and the removal of substantially all of the graphite. As a result of the calcination at a temperature greater than 600° C., the thoria catalyst had a surface area less than 62 $m^2/g$, a true density greater than 8.5 g/cc and an average crystal size greater than 75 Å.

The catalyst, both unsupported and supported, may be formed into any desired shape, formed structure, or geometric volume which may be solid or may have one or more void spaces. A void space is an unoccupied space within the solid geometric form other than pores and crevices which are normally present in a solid geometric form catalyst structure. In the description above, catalyst tablets were produced. However, other shapes or geometric forms such as, for example, spheres or spheroids, pellets, cylinders, cubes, cones, truncated cones, pyramids, truncated pyramids, prisms, star shaped cylinders and tri-lobed structures may also be used. Particularly advantageous are those geometric shapes which have a high external geometric surface area relative to the geometric volume of the structure. Suitable void spaces include grooves, holes, dimples and the like which are usually equally spaced or distributed over the external surface of the geometric form. While the shapes and void spaces may be varied greatly, the formed catalyst structure must have sufficient mechanical resistance or physical strength to withstand handling and transportation from the manufacturing point to the reactor in which it is to be used, to support its own weight within the reactor and to withstand the process conditions during its use. This may be stated as a requirement that the formed catalyst structure substantially maintain its structural integrity during manufacture, transportation and use. There are potential benefits from the use of the various possible catalyst shapes including, for example, reducing pressure drop in the reactor and reducing potential mass transfer problems, both of which can increase the catalytic conversion.

The formed catalyst structure may be produced by any suitable known method such as, for example, pressing or compacting the catalyst material into a mold, tableting by the use of a die and punch, extrusion or casting. The desired structure will determine which of the various methods are most appropriate for producing a specific structure.

Supported thoria catalysts can be made by a variety of techniques. In general the support used must have suitably neutral acid-base properties and have a relatively low surface area. Calcination of higher surface area precursors of the support material at temperatures of 500° C.–1000° C. will usually provide a support having the desired surface area. The resulting calcined support will advantageously have high porosity. Absorption from aqueous solutions of thorium salts is related to the porosity which may be measured by the "towel method" or "incipient wetness techniques".

In one method for producing the supported thoria catalyst, a water paste of fumed silica from J. L. Cabot Company, the desired support material, is dried at a temperature of about 120° C. and calcined at an elevated temperature. The calcined support was impregnated with thoria by contact with a 40% by weight aqueous solution of thorium nitrate tetrahydrate for at least 10 minutes. The impregnated support particles are dried at about 120° C. and then calcined for a period of at least about 6 hours, in accordance with this invention, at a temperature greater than about 600° C., preferably greater than about 650° C. and more preferably greater than 700° C. in the same manner as the calcining of the unsupported thoria catalyst. The thoria containing composite is passed through a sieve to obtain a catalyst having particle sizes of about 40 mesh. The smaller the catalyst particle size, the higher the expected catalyst activity for use in a process for the conversion of phenol to diphenyl oxide. The thorium content of the supported catalyst, as thorium oxide ($ThO_2$), will be about 40% by weight of the catalyst and the thoria portion of the supported catalyst will have a surface area less than 62 $m^2/g$, a true density greater than 8.5 g/cc and an average crystal size greater than 75 Å. Catalyst activity for the conversion of phenol to diphenyl oxide increases with temperature in the temperature range of from about 400° C. to about 475° C. and usually will increase with increasing thoria content in the catalyst in the range of from about 1% to about 75% thoria by weight of the catalyst.

Other methods for producing the supported thoria catalyst may be used. A thoria precursor material with a high surface area can be physically mixed with a suitable support material and the mixture can be formed to the desired geometrical shape before being calcined. In another method, the "wash coating" method, a slurry of thorium containing material is mixed with a desired support material which has a low surface area such as, for example, alpha-alumina, silicon-carbide and mullite and monolithic structures such as cordierite or beta spodumene before the slurry is dried, formed and calcined. Alternatively, the thoria precursor and the selected support material may be precipitated together and then formed into the desired geometric shape before calcining.

In the examples below, the conversion rate for the conversion of phenol to diphenyl oxide was determined by placing a 50 gram portion of each catalyst in a differential flow reactor. The reactor consisted of two concentric tubes, a 1.27 cm diameter, 316 stainless steel inner tube and a 1.90 cm diameter, 316 stainless steel outer tube. The tube wall thicknesses were 0.165 cm and 0.125 cm respectively. The catalyst was placed within the inner tube and regenerated by heating from 400° C. to 540° C. over a period of 2 hours while continuously flowing a gas steam through the catalyst bed. The composition of the gas at the beginning of the regeneration was 1% $O_2$/99% $N_2$ and it was varied during the regeneration period until the composition of the gas at the end of the regeneration was 5% $O_2$/95% $N_2$. Catalyst bed temperatures during the regeneration were kept below 540° C.

The temperature of the catalyst bed was lowered to about 400° C. before the phenol feed was initiated. Phenol was fed from a tank, maintained at 65° C., which contained a nitrogen sparge. Liquid phenol was pumped to a heated zone and vaporized, exiting the vaporizer at a temperature greater than 200° C., without the use of diluent gases. The phenol was further heated to a temperature of about 300° C. before it was fed into the reactor. The phenol vapor entered the outer tube of the reactor at the top, passed downward between the two tubes, and passed upward through the catalyst bed in the inner tube before exiting from the reactor. Phenol flow rates were varied from about 30 grams/hour to about 120 grams/hour. Temperatures within the catalyst bed were varied between 400° C. and 475° C.

The reaction product was collected at the exit from the reactor and analyzed to determine the conversion of phenol to diphenyl oxide. water in the product was analyzed by the Karl Fisher Method and the results of the analysis for phenol and diphenyl oxide were corrected for the amount of water present. The conversion rates for the examples below are shown in the Table with the physical properties of the catalysts.

The invention will be explained in detail in accordance with the examples below, which are for illustrative purposes only and shall not limit the present invention. Some of the catalyst prepared in the examples below was prepared in laboratory equipment and the remainder was prepared in commercial scale equipment. Laboratory equipment consists of small furnaces and, as a result, only small batches of catalyst are prepared, thus, temperature control within the furnace is relatively precise. Similar control of temperature within commercial scale equipment is difficult and temperature variations often occur within different portions of commercial furnaces. Other factors also differ between laboratory and commercial scale equipment including some of the operating parameters. In commercial furnaces, for example, direct firing of the catalyst is employed for calcination and the combustion gases pass over the catalyst. In the laboratory, in contrast, the gas mixture passing over the catalyst is heated air which is much cleaner than the combustion gases and water, carbon monoxide and carbon dioxide are not present. Therefore, during the calcination of catalyst in commercial furnaces, an effective calcination temperature must be considered rather than the measured temperature which depends upon the placement of the measurement devices and the location of the catalyst within the furnace. The effective calcination temperature is the temperature necessary to produce the physical properties desired for the catalyst of this invention which result from a time and temperature history in the furnace. Correlations can be developed for any of the three physical properties listed in the Table for Examples 2, 3 and 5–7 to relate that property to the actual measured laboratory calcination temperature. This correlation can be used to determine the effective calcination temperature for the catalysts of Examples 4 and 8–11 which were prepared in commercial furnaces. If the measured average thoria crystal size is considered, for example, the effective calcination temperature is calculated by taking a linear regression of the measured calcination temperature (x-variable) against the measured thoria crystal size (y-variable) in Examples 2, 3 and 5–7. In the examples which used commercial scale furnaces in which the temperature of the calcination was unknown or imprecise, Examples 4 and 8–11, the effective calcination temperature can be determined from the correlation developed from the measured values in Examples 2, 3 and 5–7. The effective calcination temperatures are shown in parenthesis in the Table.

EXAMPLE 1

Unsupported thoria catalyst tablets were prepared. A high surface area thorium oxalate was prepared by the precipitation of the oxalate salt and the precipitate was oven dried at 120° C. The high surface area oxalate material (Area>62 $m^2/g$) was mixed with 1.5% by weight graphite and the thoria-graphite composite was formed into cylindrical tablets having a diameter and a length of about 4.75 mm. The catalyst at this uncalcined stage of preparation is termed a 'green' catalyst. This is a poor catalyst. The physical properties of the 'green' catalyst and the conversion rate for the conversion of phenol to diphenyl oxide when this catalyst was used at a process temperature of 420° C. are shown in the Table.

EXAMPLES 2–3

The 'green' catalyst tablets of Example 1 were air calcined in a laboratory furnace at temperatures of 550° C. and 700° C. The temperature was raised to the desired calcination temperature at a heating rate of about 1° C./minute and the temperature was held at the desired temperature for about 5 hours. The physical properties of these catalyst samples and the conversion rates for the conversion of phenol to diphenyl oxide when these catalysts were used at a process temperature of 420° C. are shown in the Table.

EXAMPLE 4

The 'green' catalyst tablets of Example 1 were calcined in commercial equipment at an effective calcination temperature of 591° C. The temperature was raised to the desired calcination temperature at a heating rate of about 1° C./minute and the temperature was held at the desired temperature for about 5 hours. This catalyst was relatively poor. The physical properties of this catalyst sample and the conversion rate for the conversion of phenol to diphenyl oxide when this catalyst was used at a process temperature of 420° C. are shown in the Table.

EXAMPLES 5–7

The catalyst tablets calcined in commercial scale equipment at an effective calcination temperature of 591° C. in Example 4 were further air calcined at temperatures of 600° C., 722° C. and 822° C. in a laboratory furnace. The temperature was raised to the desired calcination temperature at a heating rate of about 1° C./minute and the temperature was held at the desired temperature for about 5 hours. The physical properties of these catalysts and the conversion rates for the conversion of phenol to diphenyl oxide when these catalysts are used at a process temperature of 420° C. are shown in the Table.

EXAMPLE 8

The catalyst tablets calcined in commercial scale equipment at an effective calcination temperature of 591° C. in Example 4 were further calcined in commercial scale equipment at an effective calcination temperature of 652° C. The temperature was raised to the desired calcination temperature and the temperature was held at the desired temperature for about 5 hours. The physical properties of this catalyst and the conversion rate for the conversion of phenol to diphenyl oxide when this catalyst is used at a process temperature of 420° C. are shown in the Table.

EXAMPLES 9–11

Additional thoria tablets were prepared from thorium oxalate as described in Example 1. The thoria tablets were calcined in commercial scale equipment in accordance with the general procedure described in Examples 2–3 in which the temperature was raised to the desired calcination temperature at a heating rate of about 1° C./minute and the temperature was held at the desired temperature for about 5 hours. The physical properties of these catalysts, the effective calcination temperatures and the conversion rates for the conversion of phenol to diphenyl oxide when these catalysts are used at a process temperature of 440° C. are shown in the Table.

EXAMPLE 12

A supported thoria catalyst was prepared using 100 grams of alpha alumina from Norton Company. The support was in the form of spheres having a diameter of about 3.2 mm with a composition of 87% alumina and 13% silica, a porosity of 40–45% and a surface area of 0.02–0.08 $m^2/g$. The water absorptivity was 13.1 g/100 g of support and was measured by the towel method. A saturated solution of thorium nitrate tetrahydrate was used to wet or impregnate the support. The wetted material was dried at 120° C. and air calcined. During the calcination, the temperature was raised from ambient temperature to about 700° C. at a heating rate of 1° C./minute and held at that temperature for about 5 hours. The impregnation, drying and calcining steps may be repeated to increase the thoria content of the supported catalyst. The thorium content of the finished supported catalyst varied from about 5% to about 20% thoria by weight of the catalyst. Conversion of phenol to diphenyl oxide was proportional to the thoria content of the catalyst.

TABLE

| | | Physical Properties | | | |
|---|---|---|---|---|---|
| Example | Calcining Temp (° C.) | Surface Area ($m^2/g$) | True Density (g/cc) | Average Crystal Size (Å) | Conversion To DPO (%) |
| 1 | uncalcined | 78 | 7.618 | 51 | 23.5 |
| 2 | 550 | 70 | 8.519 | 67 | 31.1 |
| 3 | 700 | 45 | 8.821 | 95 | 33.7 |
| 4 | (591) | 72.1 | 8.350 | 68 | 29.5 |
| 5 | 600 | 62.9 | 8.744 | 73 | — |
| 6 | 722 | 39.6 | 8.933 | 90 | — |
| 7 | 822 | 19.2 | 9.257 | 174 | 36.4 |
| 8 | (652) | 43.4 | 8.806 | 90 | 37.6 |
| 9 | (632) | 63.2 | 8.45 | 83 | 37.8 |
| 10 | (671) | 52.6 | 8.66 | 97 | 42.2 |
| 11 | (588) | 67.7 | 8.44 | 67 | 40.0 |

It will be apparent from the examples that many other variations and modifications may be made in the compositions and processes described without departing from the concept and spirit of the invention. Accordingly, it should be understood that the description and examples are illustrative only and are not intended to limit the scope of the invention.

We claim:

1. An unsupported thoria catalyst useful for the production of diaryl ethers from aromatic compounds, wherein said thoria catalyst is prepared from a high surface area thoria precursor, and wherein said thoria catalyst has a surface area less than 62 m2/g, a true density greater than 8.5 g/cc and an average crystal size greater than 75 angstroms.

2. An unsupported thoria catalyst for the production of diaryl ethers from aromatic compounds comprising thoria having a surface area less than 62 $m^2/g$, a true density greater than 8.5 g/cc and an average crystal size greater than 75 angstroms.

3. The thoria catalyst of claim 2 wherein the thoria has a surface area less than 60 $m^2/g$.

4. The thoria catalyst of claim 3 wherein the thoria has a surface area less than 55 $m^2/g$.

5. The thoria catalyst of claim 2 wherein the thoria has a true density greater than 8.6 g/cc.

6. The thoria catalyst of claim 2 wherein the thoria has an average crystal size greater than 90 angstroms.

7. The thoria catalyst of claim 2 wherein the thoria has a surface area less than 55 $m^2/g$, a true density greater than 8.6 g/cc and an average crystal size greater than 90 angstroms.

8. An unsupported catalyst for conversion of hydroxy-substituted aromatic compounds to diaryl ethers comprising thoria having a surface area less than 62 $m^2/g$, a true density greater than 8.5 g/cc and an average crystal size greater than 75 angstroms.

9. A process for producing a thoria catalyst useful for the production of diary ethers from aromatic compounds, wherein said thoria catalyst has a surface area less than 62 m2/g, a true density greater than 8.5 g/cc and an average crystal size greater than 75 angstroms, comprising the steps of (a) preparing a formed thoria structure from a high surface area thoria precursor and (b) calcining the formed thoria structure at a temperature greater than about 600° C.

10. The process of claim 9 in which the formed thoria structure is calcined at a temperature greater than about 650° C.

11. The process of claim 10 in which the formed thoria structure is calcined at a temperature greater than about 700° C.

12. The process of claim 9 wherein the thoria has a surface area less than 60 $m^2/g$.

13. The process of claim 12 wherein the thoria has a surface area less than 55 $m^2/g$.

14. The process of claim 9 wherein the thoria has a true density greater than 8.6 g/cc.

15. The process of claim 9 wherein the thoria has an average crystal size greater than 90 angstroms.

16. The process of claim 9 wherein the thoria has a surface area less than 55 $m^2/g$, a true density greater than 8.6 g/cc and an average crystal size greater than 90 angstroms.

17. A supported thoria catalyst useful for the production of diaryl ethers from aromatic compounds, comprising a support material and a thoria portion, wherein said thoria portion is prepared from a high surface area thoria precursor, and wherein the thoria portion of said thoria catalyst has a surface area less than 62 m2/g, a true density greater than 8.5 g/cc and an average crystal size greater than 75 angstroms.

18. The supported thoria catalyst of claim 17 wherein the support material is selected from the group consisting of alpha-alumina, pure silica, pure zirconia, carbon, asbestos, quartz, silicon carbide, cordierite, mullite and beta spodumene.

19. The supported thoria catalyst of claim 17 wherein the thoria portion has a surface area less than 60 $m^2/g$.

20. The supported thoria catalyst of claim 19 wherein the thoria portion has a surface area less than 55 $m^2/g$.

21. The supported thoria catalyst of claim 17 wherein the thoria portion has a true density greater than 8.6 g/cc.

22. The supported thoria catalyst of claim 17 wherein the thoria portion has an average crystal size greater than 90 angstroms.

23. The supported thoria catalyst of claim 17 wherein the thoria portion has a surface area less than 55 $m^2/g$, a true density greater than 8.6 g/cc and an average crystal size greater than 90 angstroms.

24. A catalyst for conversion of aromatic compounds to diaryl ethers comprising a supported thoria catalyst having a thoria portion, the thoria portion having a surface area less than 62 m²/g, a true density greater than 8.5 g/cc and an average crystal size greater than 75 angstroms.

25. A process for the production of a supported thoria catalyst useful for the production of diaryl ethers from aromatic compounds, comprising the steps of (a) preparing a support, (b) combining a high surface area thoria precursor with the support, (c) drying the combined support and thoria precursor and (d) calcining the combined support and thoria precursor at a temperature greater than about 600° C. for sufficient time to produce said supported thoria catalyst, having a thoria portion with a surface area less than 62 m2/g, a true density greater than 8.5 g/cc and an average crystal size greater than 75 angstroms.

26. The process of claim 25 wherein preparing the support comprises the steps forming a support structure and calcining the formed support structure at an elevated temperature.

27. The process of claim 25 wherein the combined support and thoria precursor are calcined at a temperature greater than about 650° C.

28. The process of claim 27 wherein the combined support and thoria precursor are calcined at a temperature greater than about 700° C.

29. The process of claim 25 wherein the thoria portion has a surface area less than 60 m²/g.

30. The process of claim 29 wherein the thoria portion has a surface area less than 55 m²/g.

31. The process of claim 25 wherein the thoria portion has a true density greater than 8.6 g/cc.

32. The process of claim 25 wherein the thoria portion has an average crystal size greater than 90 angstroms.

33. The process of claim 25 wherein the thoria portion has a surface area less than 55 m²/g, a true density greater than 8.6 g/cc and an average crystal size greater than 90 angstroms.

34. A method for producing diaryl ethers comprising passing an aromatic compound over a supported thoria containing catalyst having a thoria portion, wherein said thoria portion is prepared from a high surface area thoria precursor and wherein said thoria portion has a surface area less than 62 m2/g, true density greater than 8.5 g/cc and an average crystal size greater than 75 angstroms at a temperature between about 400° C. and about 475° C.

35. The method for producing diaryl ethers of claim 34 wherein the thoria portion has a surface area less than 55 m²/g, true density greater than 8.6 g/cc and an average crystal size greater than 90 angstroms.

36. A method for producing diaryl ethers comprising passing an aromatic compound over an unsupported thoria catalyst prepared from a high surface area thoira precursor wherein said thoria catalyst has a surface area less than 62 m²/g, a true density greater than 8.5 g/cc and an average crystal size greater than 75 angstroms at a temperature between about 400° C. and about 475° C.

37. The method for producing diaryl ethers of claim 36 wherein the thoria catalyst has a surface area less than 55 m²/g, a true density greater than 8.6 g/cc and an average crystal size greater than 90 angstroms.

* * * * *

UNITED STATES PATENT AND TRADEMARK OFFICE
CERTIFICATE OF CORRECTION

PATENT NO. : 5,925,798
DATED : July 20, 1999
INVENTOR(S) : James William Gambell; Paul Ho Liu; Rudolph Ebner It is certified that error appears in the above-identified patent and that said Letters Patent are hereby corrected as shown below:

Column 1, line 18, the word "is" should be deleted.

Column 7, line 14, the word, "water" should be replaced with the word, "Water".

Signed and Sealed this

Eighth Day of May, 2001

*Attest:*

NICHOLAS P. GODICI

*Attesting Officer*     *Acting Director of the United States Patent and Trademark Office*